United States Patent [19]

McCarthy

[11] Patent Number: 4,996,345

[45] Date of Patent: Feb. 26, 1991

[54] DIFLUOROKETONES FROM DIFLUOROACYLSILANES

[75] Inventor: Peter A. McCarthy, Pawcatuck, Conn.

[73] Assignee: Pfizer Inc., New York, N.Y.

[21] Appl. No.: 369,161

[22] Filed: Jun. 21, 1989

[51] Int. Cl.$^5$ .............................................. C07F 7/18
[52] U.S. Cl. .................................... 556/485; 549/214
[58] Field of Search ........................... 556/485; 549/214

[56] References Cited

U.S. PATENT DOCUMENTS 2,892,859  6/1959  McBee et al. ...................... 556/485
4,692,537  9/1987  McAlister ........................ 556/485 X
4,933,510  6/1990  Magnusson et al. ............. 556/485 X

OTHER PUBLICATIONS

Metcalf et al., Tet. Letters 26, 2861–2864, (1985).
Yuan et al., J. Am. Chem. Soc. 109, 8071–8081, (1987).
Gelb, M. H., J. Am. Chem. Soc. 108, 3146–3147, (1986).

*Primary Examiner*—Paul F. Shaver
*Attorney, Agent, or Firm*—Peter C. Richardson; J. Trevor Lumb; A. Dean Olson

[57] ABSTRACT

A process for the synthesis of alpha,alpha-difluoroketones from alpha,alpha-difluoroacylsilanes and intermediates therefor.

15 Claims, No Drawings

DIFLUOROKETONES FROM DIFLUOROACYLSILANES

BACKGROUND OF THE INVENTION

The present invention is directed to a process for preparing alpha,alpha-difluoroketones from alpha,alpha-difluoroacylsilanes and diazo compounds via an intermediate enolic silyl ether derivative, i.e.,

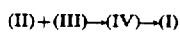

according to the formulas depicted below.

The incorporation of fluorine into organic molecules frequently effects profound changes in the biological profile of the fluorine substituted compound in comparison to the unsubstituted compound. Such changes result from the extreme electronegativity of fluorine, as well as its ability to replace hydrogen without significant steric consequences. New methods for the introduction of fluorine are thus of great interest. It follows that the alpha,alpha-difluoroketones which result from the present process are of special value as intermediates in the preparation of various medicinal agents; for example, compounds which inhibit phospholipase $A_2$. This enzyme catalyzes the liberation of arachidonic acid from the phospholipid membrane pool, the rate-determining step in the biosynthesis of prostaglandin, leukotrienes, thromboxanes and prostacyclin, compounds which play important roles in a variety of disease states; see, Gelb, J. Am. Chem. Soc., vol. 108, pp. 3146–3147 (1986), Yuan et al., ibid., vol. 109, pp. 8071–8081 (1987), and leading references there cited.

Certain alpha,alpha-difluoroketones have been previously prepared via the Claisen rearrangement of difluorovinyl ethers of allylic alcohols; Metcalf et al., Tetrahedron Letters, vol. 26, pp. 2861–2864 (1985). Many of the present alpha,alpha-difluoroacylsilane starting materials are prepared according to methods there disclosed.

SUMMARY OF THE INVENTION

The present invention is directed to a process for the preparation of an alpha,alpha-difluoroketone of the formula

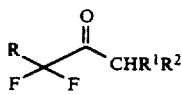

wherein

R is $(C_1-C_{20})$alkyl or $(C_2-C_{20})$alkenyl, or one of said groups substituted by phenyl or $(C_1-C_{20})$alkoxyl; and $R^1$ and $R^2$ are each independently hydrogen, $(C_1-C_{20})$-alkyl, $(C_2-C_{20})$alkenyl, phenyl or $(C_7-C_{20})$phenylalkyl; or $R^1$ is hydrogen and $R^2$ is

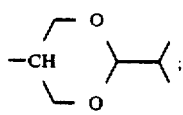

which comprises reacting an alpha,alpha-difluoroacylsilane of the formula

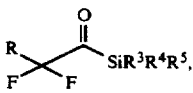

wherein $R^3$, $R^4$ and $R^5$ are each independently $(C_1-C_{20})$-alkyl, $(C_2-C_{20})$alkenyl, phenyl or $(C_7-C_{20})$-phenylalkyl; with a diazo compound of the formula

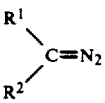

in a reaction-inert solvent at a temperature in the range of about $-20°$ C. to $100°$ C. to form an intermediate silyl ether of the formula

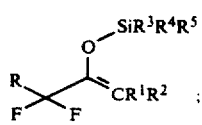

followed by hydrolysis to yield said alpha,alpha-difluoroketone of the formula (I).

The present process is particularly valuable for the preparation of difluoroketones of the formula (I) wherein R is

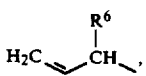

$R^1$ is hydrogen and $R^6$ is hydrogen, $(C_1-C_{17})$alkyl, phenyl or $(C_1-C_{20})$alkoxy. Particularly valuable compounds have $R^6$ as hydrogen, phenyl or $(C_1-C_{20})$alkoxy, and $R^2$ as hydrogen, $(C_1-C_{20})$alkyl or $(C_2-C_{20})$alkenyl. The preferred value of each of $R^3$, $R^4$ and $R^5$ is methyl. So as to avoid the need for pressure equipment, it is preferred to operate at a temperature at or below that of the boiling point of the particular diazo compound used in the process.

The present process is also directed to a process which further comprises conventional reduction of the ketone of the formula (I) to an alpha,alpha-difluoroalcohol of the formula

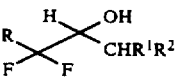

wherein R, $R^1$ and $R^2$ are as defined above; and to the intermediate compounds of the formula (IV) as defined above. Of course, when the group R contains an ester group, milder reducing agents such as $NaBH_4$ (not $LiAlH_4$) will be used in reducing the ketone to the alcohol.

The expression "reaction-inert solvent" as used above and elsewhere herein refers to a solvent which does not interact with starting materials, reagents, intermediates or products in a manner which adversely affects the yield of the desired product. So long as it meets this criteria, the solvent can be a single component or a multicomponent mixture.

DETAILED DESCRIPTION OF THE INVENTION

The present valuable process for alpha,alpha-difluoroketones is readily carried out. Thus alpha,alpha-difluoroacylsilanes of the formula (II) are simply reacted with the diazo compound (III) in a reaction-inert solvent such as diethyl ether. In general, the diazo compound is added dropwise until the yellow color of excess diazo compound persists. Temperature is not critical, with temperatures in the range of −20° to 100° C. being generally satisfactory. However, as noted above, it is preferably below the boiling point of the diazo compound so as to avoid the need for a pressure vessel in carrying out this transformation.

With or without isolation, the resulting enolic silyl ether of the formula (IV) is then conventionally hydrolyzed to produce the desired alpha,alpha-difluoroketone of the formula (I). For example, said hydrolysis is readily accomplished by contacting the silyl ether with an aqueous acid such as acetic acid or HF, or with a fluoride source, such as HF or tetrabutylammonium fluoride. A preferred reagent is HF, using at least one molar equivalent thereof, e.g., a 1% aqueous solution. This step is also generally carried out in a reaction-inert solvent; for example, aqueous tetrahydrofuran. Again, temperature is not critical; ambient temperatures, avoiding the cost of either heating or cooling, are particularly convenient.

If desired, the difluoroketone is readily converted to the corresponding alpha,alpha-difluoroalcohol by conventional means, e.g., by the use of $NaBH_4$ in a reaction-inert solvent, as exemplified below.

The required difluoroacylsilanes are readily available, for example, when R is 2-propenyl or substituted 2-propenyl, by the method of Metcalf et al. cited above. According to this method, a displaceable halide or sulfonate is reacted with 2,2,2-trifluoroethoxide, and the resulting trifluoroethyl ether is in turn reacted with LDA (lithium diisopropylamide) and then with the appropriate chlorosilane, and finally rearranged by heating to form the desired difluoroacylsilane, for example, as follows:

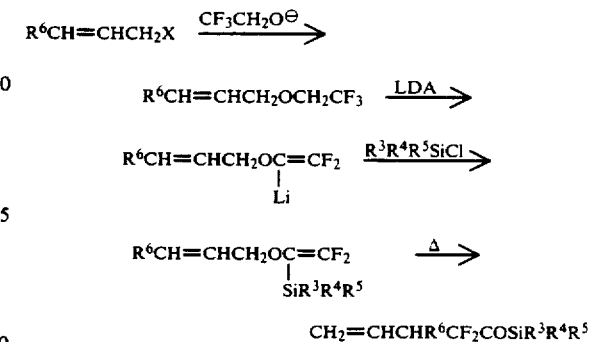

The required diazo compounds are also generally known or available by methods found in the literature. They are usually prepared from the corresponding 3-nitro-1-nitrosoguanidine in a water-immiscible, reaction-inert solvent by the action of a molar excess of an aqueous alkali metal hydroxide which is present as a second phase.

The ketones and alcohols of the formulas (I) and (V) are converted to known, useful compounds by conventional methods; for example, according to schemes 1, 2 or 3, using conventional ozonolysis or hydrogenation of the double bond, and the methods of Yuan et al. cited above to introduce alkanoyl and aminoalkyl phosphate side chains and reoxidize secondary alcohol to ketone.

The following examples illustrate but do not limit the present invention, many variations being possible within the scope and spirit thereof.

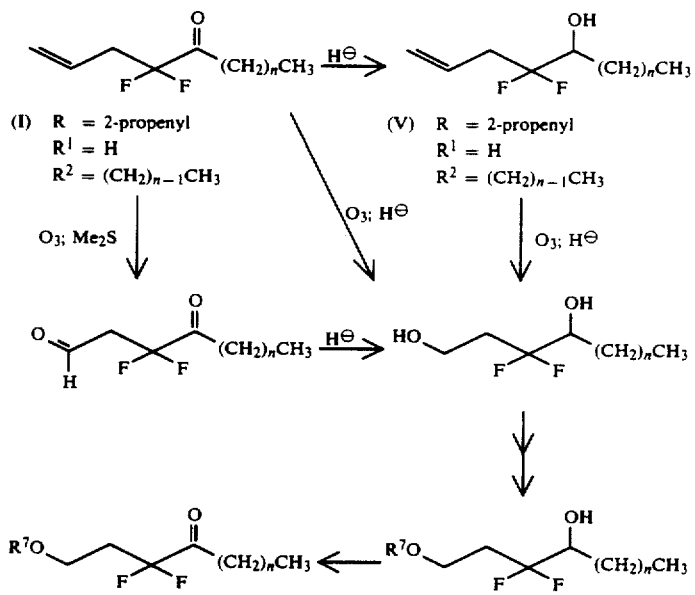

Scheme 1

Scheme 1
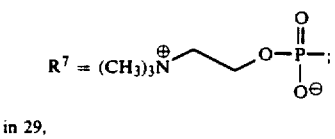
in 29,
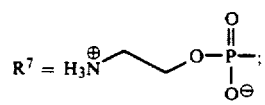
in 21, 24 and 29, n = 15; and
in 22, n = 6.
Scheme 2
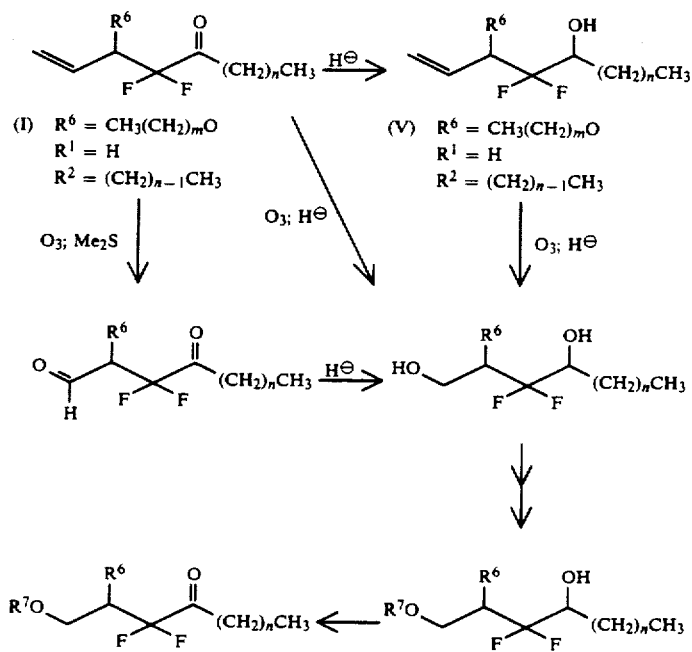
14, 23 and 30 of Yuan et al.
In 14 and 23,
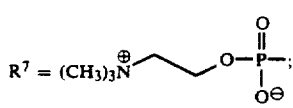
in 30,
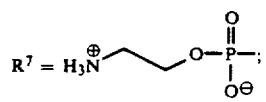
in 14, 23 and 30, $R^6 = CH_3(CH_2)_7O-$;
in 14 and 30, n = 6; and
in 23, n = 15.

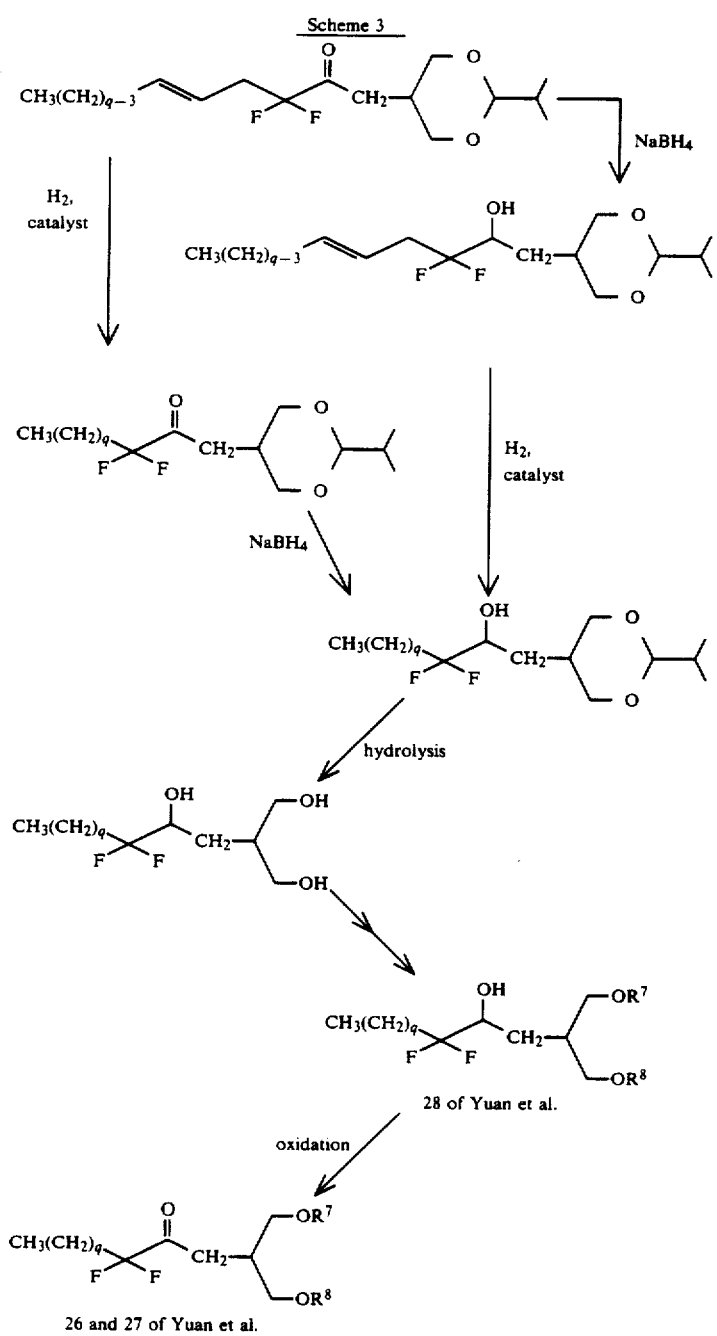

In 26, 27, and 28,

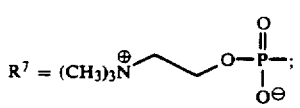

In 26, q is 5 and $R^8$ is $CH_3(CH_2)_6CO$;

In 27 and 28, q is 15 and $R^8$ is $CH_3(CH_2)_{16}CO$.

EXAMPLE 1

3,3-Difluoro-4-phenyl-2-(trimethylsilyloxy)-1,5-hexadiene

Trimethyl-(2,2-difluoro-3-phenyl-4-pentenoyl)silane (0.5 g, 1.86 mmol; prepared according to the procedures of Metcalf et al., Tetrahedron Letters, v. 26, pp. 2861–2864, 1985) was dissolved in diethyl ether (20 ml). The resulting solution was cooled to 0° C. and etheral diazomethane [prepared from 1-methyl-3-nitro-1-nitrosoguanidine (2.5 g, 317 mmole) added slowly to a two-phase mixture of aqueous KOH (4.3 g of KOH in 10 ml of water) and ethyl ether (50 ml)] was added dropwise until the yellow color persisted. The mixture was then allowed to warm to room temperature and 1 drop of glacial acetic acid was added. The mixture was concentrated in vacuo to give 593 mg (quantitative yield) of the title compound as a yellow oil.

1H-NMR(CDCl3)delta(ppm): 7.32 (m, 5H), 6.24 (ddd, 10, 12 and 20 Hz, 1H), 5.28 (d, 12 Hz, 1H), 5.17 (d, 20 Hz, 1H), 4.66 (d, 2 Hz, 1H), 4.29 (d, 2 Hz, 1H), 4.05 (dt, 10 and 16 Hz, 1H), 0.22 (s, 9H). IR (KBr) cm$^{-1}$: 2950, 1649. Mass spectrum m/e (relative intensity): M$^+$ 282 (1), 268 (4), 243 (10), 210 (35), 190 (23), 147 (23), 117 (100).

Analysis calculated for $C_{15}H_{20}F_2OSi$:
C, 63.80; H, 7.14. Found: C, 63.34; H, 7.06.

EXAMPLE 2

3,3-Difluoro-4-phenyl-5-hexen-2-one

Title product of the preceding Example (225 mg, 0.80 mmol) was dissolved in tetrahydrofuran (5 ml), and 1% aqueous HF (2 ml) was added dropwise. After stirring at room temperature for 45 minutes, the mixture was quenched with solid NaHCO3. The mixture was filtered and concentrated in vacuo to give 100 mg (60% yield) of crude product. Purification by preparative thin layer chromatography using 4:1 hexane:chloroform as eluant provides pure product as a clear oil.

1H-NMR(CDCl3)delta(ppm): 7.32 (m, 5 H), 6.18 (ddd, 10, 12 and 20 Hz, 1H), 5.34 (d, 12 Hz, 1H), 5.26 (d, 20 Hz, 1H), 4.08 (dt, 10 and 16 Hz, 1H), 2.13 (t, 2 Hz, 3H). 19F-NMR(CDCl3)delta(ppm): 68.28 (dd, 15 and 261 Hz), 65.24 (dd, 16 and 261 Hz). IR (KBr) cm$^{-1}$: 3441, 3359, 2947, 2853, 1733, 1667, 1590, 1510.

EXAMPLE 3

3,3-Difluoro-4-phenyl-5-hexen-2-ol

Title product of the preceding Example (100 mg, 0.48 mmol) was dissolved in dry tetrahydrofuran (5 ml), and a solution of sodium borohydride (10.8 mg, 285 mmol) in dry tetrahydrofuran (2.5 ml) was added dropwise at room temperature. After stirring for 4 hours, aqueous NH4Cl was added, and the phases were separated. The aqueous phase was extracted 3 times with ethyl ether, and the combined organic phases were dried, filtered and concentrated to give 92 mg (83% yield) of the title compound as a 1.6:1.0 mixture of diastereomers. 1H-NMR(CDCl3)delta(ppm): 7.38 (m, 10H), 6.30 (ddd, 10, 12 and 20 Hz, 1H), 6.24 (ddd, 10, 12 and 20 Hz, 1H), 5.35 (d, 12 Hz, 1H), 5.32 (d, 20 Hz, 1H), 5.28 (d, 12 Hz, 1H), 5.22 (d, 20 Hz, 1H), 4.03 (m, 3H), 3.68 (m, 1H), 1.80 (br s, 2H), 1.33 (s, 3H), 1.30 (s, 3H). 19F-NMR(CDCl3)delta(ppm): 60.52 (ddd, 11, 22 and 250 Hz), 59.48 (dd, 25 and 248 Hz), 57.26 (ddd, 11, 16 and 249 Hz), 56.59 (ddd, 9, 18 and 249 Hz). IR (KBr) cm$^{-1}$: 3586, 2982, 2939, 1492, 1453. Mass spectrum m/e (relative intensity): M+212 (7), 194 (10), 168 (5), 117 (100).

EXAMPLE 4

4,4-Difluoro-3-phenyl-1-decen-5-one

Trimethyl-(2,2-difluoro-3-phenyl-4-pentenoyl)silane (400 mg, 1.5 mmol) was dissolved in diethyl ether (10 ml). The resulting solution was cooled to 0° C. and etheral 1-diazopentane [prepared from 1-pentyl-3-nitro-1-nitrosoguanidine (0.6 g) added slowly to a two-phase mixture of aqueous KOH (0.67 g in 2 ml of water) and ethyl ether (10 ml)] was added dropwise. The mixture was then stirred at room temperature for 12 hours, refluxed for 0.5 hours and allowed to cool to room temperature. Excess diazopentane was destroyed and the enol ether hydrolyzed by the addition of excess aqueous acetic acid. The mixture was concentrated in vacuo to give 731 mg of crude product. This material was purified by flash chromatography using 1:4 chloroform:hexane as eluant. Pure fractions were combined and concentrated to provide 99 mg (24% yield) of title product as a viscous yellow oil. 1H-NMR(CDCl3)delta(ppm): 7.32 (m, 5H), 6.16 (ddd, 10 12 and 20 Hz, 1H), 5.32 (d, 12 Hz, 1H), 5.24 (d, 20 Hz, 1H), 4.06 (dt, 10 and 16 Hz, 1H), 2.50 (dt, 7 and 17 Hz, 1H), 2.28 (dt, 5 and 17 Hz, 1H), 1.45 (m, 2H), 1.16 (m, 4H), 0.84 (t, 6 Hz, 3H). 13C-NMR(CDCl3)delta(ppm): 134.87, 132.03, 129.51, 128.70, 127.93, 120,62, 120.40, 117.25, 114.00, 53.27, 52.98, 52.67, 37.86, 30.85, 22.24, 21.93, 13.79. IR (CDCl3) cm$^{-1}$: 2925, 1739. Mass spectrum m/e (relative intensity): M+276.1 (1).

Analysis calculated for $C_{16}H_{20}F_2O$: C, 72.16; H, 7.57. Found: C, 71.49; H, 7.67.

By the same method, the following additional compounds are prepared from the appropriate trimethyl-(acyl)silane and diazoalkane:
4,4-difluoro-3-(octyloxy)-1-henicosen-5-one;
4,4-difluoro-3-(octyloxy)-1-dodecen-5-one;
4,4-difluoro-3-(isobutyloxy)-1-octen-5-one;
4,4-difluoro-3-(pentanoyloxy)-1-decen-5-one;
4,4-difluoro-7-phenyl-1-hepten-5-one;
5,5-difluoro-6-dodecanone;
4,4-difluoro-2-methyl-3-heptanone; and
3,3-difluoro-4-methyl-2-heptanone.

EXAMPLE 4 alpha,alpha-Difluoroalkanols

By the method of Example 3, the difluoroalkanone derivatives of the preceding Example are converted to:
4,4-difluoro-3-phenyl-1-decen-5-ol;
4,4-difluoro-3-(octyloxy)-1-henicosen-5-ol;
4,4-difluoro-3-(octyloxy)-1-dodecen-5-ol;
4,4-difluoro-3-(isobutyloxy)-1-octen-5-one;
4,4-difluoro-3-(pentanoyloxy)-1-decen-5-ol;
4,4-difluoro-7-phenyl-1-hepten-5-ol;
5,5-difluoro-6-dodecanol;
4,4-difluoro-2-methyl-3-heptanol; and
3,3-difluoro-4-methyl-2-heptanone.

I claim:
1. A silyl ether of the formula

(IV)

wherein
R is (C1–C20)alkyl or (C2–C20)alkenyl, or one of said groups substituted by phenyl or (C1–C20)alkoxyl;
R1 and R2 are each independently hydrogen, (C1–C20)alkyl, (C2–C20)alkenyl, phenyl or (C7–C20)phenylalkyl; or R1 is hydrogen and R2 is

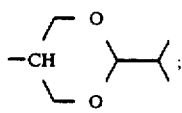

and $R^3$, $R^4$ and $R^5$ are each independently $(C_1-C_{20})$alkyl, $(C_2-C_{20})$alkenyl, phenyl or $(C_7-C_{20})$phenylalkyl;

2. A compound of claim 1 wherein R is

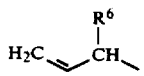

wherein $R^6$ is hydrogen, $(C_1-C_{17})$alkyl, phenyl or $(C_1-C_{20})$alkoxy.

3. A compound of claim 2 wherein $R^1$ and $R^6$ are each hydrogen.

4. A compound of claim 3 wherein $R^3$, $R^4$ and $R^5$ are each methyl and $R^2$ is $(C_1-C_{20})$alkyl.

5. The compound of claim 4 wherein $R^2$ is $-(CH_2)_5CH_3$.

6. The compound of claim 4 wherein $R^2$ is $-(CH_2)_{14}CH_3$.

7. A compound of claim 2 wherein $R^1$ is hydrogen and $R^6$ is $(C_1-C_{20})$alkoxy.

8. A compound of claim 7 wherein $R^3$, $R^4$ and $R^5$ are each methyl and $R^2$ is $(C_1-C_{20})$alkyl.

9. The compound of claim 8 wherein $R^6$ is $CH_3(CH_2)_7O$ and $R^2$ is $-(CH_2)_5CH_3$.

10. The compound of claim 8 wherein $R^6$ is $CH_3(CH_2)_7O$ and $R^2$ is $-(CH_2)_{14}CH_3$.

11. A compound of claim 2 wherein $R^1$ is hydrogen and $R^6$ is phenyl.

12. A compound of claim 11 wherein $R^3$, $R^4$ and $R^5$ are each methyl and $R^2$ is hydrogen, $(C_1-C_{20})$alkyl or $(C_2-C_{20})$alkenyl.

13. The compound of claim 12 wherein $R^2$ is hydrogen.

14. The compound of claim 12 wherein $R^2$ is $-(CH_2)_3CH_3$.

15. The compound of claim 12 wherein $R^2$ is $-CH_2)_6CM=CH(CH_2)^7CH_3$.

* * * * *

UNITED STATES PATENT AND TRADEMARK OFFICE
CERTIFICATE OF CORRECTION

PATENT NO. : 4,996,345

DATED : February 26, 1991

INVENTOR(S) : Peter A. McCarthy

It is certified that error appears in the above-identified patent and that said Letters Patent is hereby corrected as shown below:

Column 12, line 6, "$CH_3(CH_2)^7O$" should read -- $CH_3(CH_2)_7O$ --.

Column 12, line 19, "$-CH_2)_6CM=CH(CH_2)^7CH_3$" should read -- $-(CH_2)_6CH=CH(CH_2)_7CH_3$ --.

Column 11, line 2, replace ; with a period at end of sentence.

Signed and Sealed this

Tenth Day of November, 1992

Attest:

DOUGLAS B. COMER

Attesting Officer

Acting Commissioner of Patents and Trademarks